United States Patent
Rao (10) Patent No.: US 7,469,213 B1
(45) Date of Patent: Dec. 23, 2008

(54) PRESCRIPTION DRUG DISTRIBUTION SYSTEM AND METHODS

(75) Inventor: John Rao, Tempe, AZ (US)

(73) Assignee: Secure Medical, Inc., Tempe, AZ (US)

( * ) Notice: Subject to any disclaimer, the term of this patent is extended or adjusted under 35 U.S.C. 154(b) by 839 days.

(21) Appl. No.: 10/389,363

(22) Filed: Mar. 14, 2003

(51) Int. Cl.
G06Q 50/00 (2006.01)
(52) U.S. Cl. ............................................. 705/2; 705/3
(58) Field of Classification Search ................ 705/2–4; 600/300
See application file for complete search history.

(56) References Cited

U.S. PATENT DOCUMENTS

| | | | |
|---|---|---|---|
| 5,502,944 A | 4/1996 | Kraft et al. | |
| 5,597,995 A | 1/1997 | Williams et al. | |
| 5,842,976 A | 12/1998 | Williamson | |
| 5,907,493 A | 5/1999 | Boyer et al. | |
| 5,970,462 A | 10/1999 | Reichert | |
| 6,032,155 A | 2/2000 | de la Huerga | |
| 6,046,761 A | 4/2000 | Echerer | |
| 6,202,923 B1 | 3/2001 | Boyer et al. | |
| 6,234,343 B1 | 5/2001 | Papp | |
| 6,438,451 B1 | 8/2002 | Lion | |
| 6,687,676 B1 * | 2/2004 | Denny ........................... | 705/2 |
| 2002/0077841 A1 | 6/2002 | Thompson | |
| 2002/0082745 A1 | 6/2002 | Wilmott et al. | |
| 2002/0100762 A1 | 8/2002 | Liff et al. | |
| 2002/0111832 A1 | 8/2002 | Judge | |
| 2002/0143434 A1 | 10/2002 | Greeven et al. | |
| 2002/0147615 A1 | 10/2002 | Doerr et al. | |
| 2002/0173875 A1 | 11/2002 | Wallace et al. | |
| 2002/0176610 A1 * | 11/2002 | Okazaki et al. ............. | 382/118 |
| 2003/0018495 A1 * | 1/2003 | Sussman ........................ | 705/2 |
| 2004/0024614 A1 * | 2/2004 | Alexander et al. ............. | 705/2 |

OTHER PUBLICATIONS

Holme, C. "Whizz-kid's Prescription for Future: Just What the Doctor Ordered." The Herald. Glasgow (UK): Dec. 29, 1999. p. 3.*
"Handymedical.com Launches Online Printable Evergency Service." PR Newswire. Wednesday, Feb. 12, 2003.*

* cited by examiner

Primary Examiner—Thomas Dixon
Assistant Examiner—Martin A Gottschalk
(74) Attorney, Agent, or Firm—Booth Udall, PLC (57) ABSTRACT

Secure methods of distributing and prescribing prescription medications and related systems significantly increase prescription medication distribution security. Applications of the present invention are particularly useful in prescribing and distributing lifestyle drugs where an actual physical examination is not necessarily required, but are similarly useful for all prescription medications. A system configured according to a particular embodiment of the present invention involves a prescription request kiosk, a prescription request review terminal, a medical information database, and a pharmacy all associated with a prescription distribution system processor. Particular embodiments of prescriptions of the present invention include a photograph of a prescription requestor on the prescription for added security along with additional follow-up questions to be asked by the pharmacist to the customer. Requestors initiate prescription requests by answering a plurality of questions related specifically to the prescription medications requested.

13 Claims, 5 Drawing Sheets

PRESCRIPTION DRUG DISTRIBUTION SYSTEM AND METHODS

BACKGROUND OF THE INVENTION

1. Technical Field

This invention relates generally to methods for distributing prescription drugs. It relates more specifically to secure methods and systems for issuing and filling prescriptions.

2. Background Art

With the advent of mail order and online ("cyber-") pharmacies accessible via the Internet, most all medically prescribed prescription, as well as non-prescription drugs and general health & beauty aids can be shipped to the customer within 2-5 days by regular mail or overnight by an express courier service for a price. While such modes of delivery may be satisfactory in many situations, there are situations in which the applicable time delay is inconvenient for a customer.

There is a group of prescription drugs known in the industry as "lifestyle" drugs which are not necessary for the health of the patient, but may improve the quality of life for the patient. Some examples of lifestyle drugs include, but are not limited to, drugs for weight loss, hair loss, erectile dysfunction, pain relief from arthritis, allergies, herpies, birth control, skin care, smoking, and the like. The lifestyle drugs can often be prescribed by a doctor without an actual physical examination of the patient. As such, these drugs have found significant popularity for ordering through the Internet. Numerous cyber-pharmacies have been established wherein a customer researches and selects a desired drug, requests a prescription, answers questions posed by an online doctor, and is granted a prescription for the requested drug. The prescription drug is then shipped to the address provided by the customer requesting the drug.

Although prescription lifestyle drugs are not necessary for the health of the patient, they are, nonetheless, "prescription" drugs and regulation of the drugs is still a concern. For example, the well known erectile dysfunction drug Viagra® is a popular street drug and has side effects which can pose significant health and public safety risks if taken by someone with particular health problems or someone taking other common conflicting drugs. Abuse of the cyber-pharmacy system can arise from dishonest consumers obtaining duplicate prescriptions to various pharmacies, perhaps under a plurality of false identities, or by answering the questions posed to them dishonestly, acquiring the drugs and selling them on the street.

Due to the ease by which a customer can receive prescriptions for prescription drugs, many cyber-pharmacies have come under attack for the apparent lack of controls associated with prescriptions and prescription drugs being distributed through cyber-pharmacies. Similar complaints, however, could be made of walk-in clinics where a customer pays cash and can walk into a number of clinics to obtain a variety of prescriptions for the same drug. Despite the numerous safety protocols instituted by cyber-pharmacies to overcome the concerns, the verbal, written and legal attacks continue. Concern has also been expressed by cyber-pharmacy customers that the drugs they are ordering are, perhaps, not the highest of quality, that the customer's medical information is not going to be kept private, and that the customer's credit card information is at risk.

Conventionally, a prescription from a doctor includes the name of the clinic from which the prescription was issued, a name of the patient for whom the drug was prescribed, a signature of the doctor, a date for the prescription, a name and dosage of the drug prescribed, and perhaps an indication for the number of refills prescribed. Anyone carrying the prescription to the pharmacy and paying for the drugs can collect the prescription drug. Conventionally, the pharmacist's interaction with the customer, despite the significant education required to become a pharmacist, involves reading the dosage on the bottle to the customer and collecting the customer's money.

Accordingly, what is needed is a system for distributing prescription drugs which allows for the convenience of cyber-pharmacies, yet provides security so that only the intended recipient receives the drugs and is limited as to how much of the drug the recipient is permitted to obtain.

DISCLOSURE OF THE INVENTION

The present invention relates to secure methods and systems for distributing prescription drugs. Aspects of the invention include systems and methods for confirming the identity of the medication requestor, confirming that the medication requester actually needs and would benefit or continue to benefit from the medication, prevention of abusers of the prescription system, and providing convenient prescription drugs. While particular embodiments of the present invention are particularly useful for use with lifestyle drugs, it will be clear that other embodiments of the invention will also be useful for other types of prescription drugs. In particular embodiments, a photograph of a requestor of a prescription drug is taken while the requester is asking for the drug and filling out a questionnaire. When the prescription is delivered to the requester either at a pharmacy or by shipment to the requestor's home, the photograph is compared with the requestor's face and additional identification is requested. Credit card information may also be used to confirm the identity of the requester.

While requesting the prescription, the requestor is also asked a series of questions related specifically to the prescription drug requested. When the requestor picks up the prescription at the pharmacy, the pharmacist asks follow-up questions to ensure the prescription is right for the requestor. Refills are not automatically granted, but are issued only after an additional request by the requester for a refill. Questions specific to refills of the requested prescription are asked.

The photographs and information given by each requester, along with information relating to the prescription and its use, are stored in a medical information database for future reference in issuing prescriptions and distributing medication. When subsequent prescriptions are requested, comparison may be made with previous information and even the photographs taken to determine if the requester using the name and address is the same as previously used that name and address.

By having numerous layers of security, the safety with which prescription medication is distributed will increase significantly. Customers will be more satisfied with the results they obtain from their prescription drugs, and more satisfied with the convenience of ordering and receiving their prescriptions in a convenient place in a short amount of time. Retail establishments will be more satisfied with the greater number of customers coming into their stores to order pharmaceuticals because the customers will also purchase other products.

By relying more upon the vast knowledge of the pharmacists to safeguard against customers improperly or wrongly receiving prescription medications, pharmacists will be more satisfied with their work, and greater customer safety may be employed. The methods and systems of the present invention, if used, will also significantly decrease the amount of prescription medication which shows up on the street due to prescription fraud.

The foregoing and other features and advantages of the present invention will be apparent from the following more detailed description of the particular embodiments of the invention, as illustrated in the accompanying drawings.

DETAILED DESCRIPTION OF EMBODIMENTS OF THE INVENTION

As discussed above, embodiments of the present invention relate to secure methods for distributing prescription medications through the use of a photograph of the person requesting the prescription, requesting additional medical information at the time of the prescription pickup, and a prescription kiosk. Through use of embodiments of the present invention, security in distributing prescription medications is significantly increased both for lifestyle medications, such as those conventionally distributed without a physical examination to customers ordering through the Internet, as well as for other conventional prescription medications.

Figure 1:
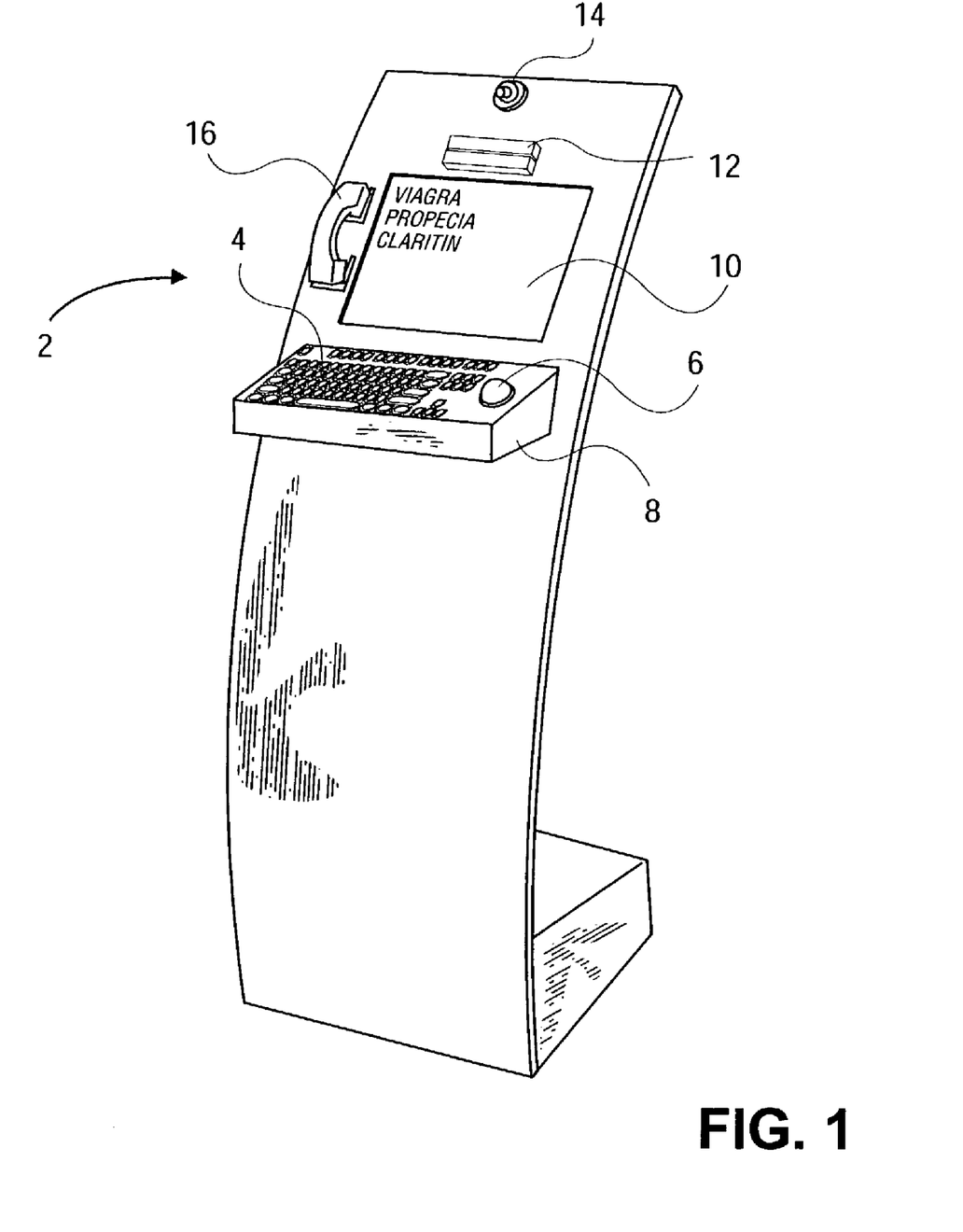
FIG. 1 is a perspective view of a prescription request interface terminal configured according to an embodiment of the present invention.

FIG. 1 illustrates one example of a prescription request interface terminal 2 or kiosk 2 configured according to an embodiment of the invention. Kiosks having connection to a computer network or for connection to the Internet are known in the art and are available for purchase through kiosk companies such as Affordable Kiosks on the Internet at affordablekiosks.com. Conventional kiosks include an input device such as a computer keyboard 4, which may also include a cursor controller 6 such as a mouse, touchpad or track ball, supported by a keyboard support 8. The kiosk 2 of the present invention also includes a display 10, a credit card reader 12, a camera 14 and a telephone handset 16.

The display 10 may be of a kind typical to kiosks for viewing images transmitted to the display 10. Additionally, as is common with kiosks, the display 10 may be a touch sensitive screen for interacting with the kiosk 2. In particular embodiments using a touch screen, it may not be necessary to include a keyboard because simple interaction may be accomplished through the touch screen. In other embodiments, however, both a touch sensitive display 10 and a keyboard 4 and/or a cursor controller 6, will be used in combination to enable interaction. The telephone handset 16, or some other form of verbal interaction or sound receiving and/or transmitting device (e.g. a speaker or microphone on the kiosk), may be used to enable the requester or other customer to verbally interact with a person or system associated with the kiosk 2. It will be understood to those of ordinary skill in the art that instructions may be given and questions asked to the customer through either the display 10 or the handset 10, and that answers may be given by the customer through the handset 10 or through a touch screen display 10 or keyboard 4. Numerous combinations of interaction using these interaction tools may also be used to accomplish the purposes of the present invention. The handset 16, however, gives the particular ability to enable easy interaction with the system or a live person, such as a pharmacist, doctor, or help desk, to ask questions, or for the doctor or pharmacist to ask additional questions to the customer.

The camera 14 is included in the prescription drug request interface terminal 2 of embodiments of the present invention to capture an image of the requestor of a prescription drug proximate the time the requestor requests the prescription. Capturing an image of the requester of the prescription may be accomplished in a number of ways known to those of ordinary skill in the art and may include, without limitation, stationary or moving digital or analog photography as well as other forms of capturing an image of the requestor. As used herein, capturing an image of the requestor "proximate" the time the requestor requests the prescription means capturing the image of the requester at or around the time the requestor requests the prescription and/or reviews the information at the terminal, and does not include capturing an image of the requestor which was taken at a previous time, such as a drivers license photo, or merely transferring a previously captured image of the requester on file. The picture feature of the invention is intended to provide added security and, therefore, should be an image of the actual requester of the prescription medication. As used herein, "drug" and "medication" are used interchangeably.

The prescription request interface terminal 2 also includes a power supply (not shown) to supply power to the terminal 2, and a network connection (also not shown) to enable the transfer of data to and from the terminal 2. Power supplies may include, for example, a plug plugged into a standard outlet, or may include a battery or other power supply which does not require external connection. Similarly, the network connection to the terminal 2 may include a direct connection to a data source, such as through a co-axial telephone, network or other cable connection, or may include, without limitation, a wireless connection, such as through Bluetooth transmissions, cellular transmissions, radio or other frequency transmissions, and the like. Power and network connection possibilities and configurations are well known in the art and those of ordinary skill in the art will readily be able to properly configure embodiments of the present invention for power and network connection from the description provided herein.

Figure 2:
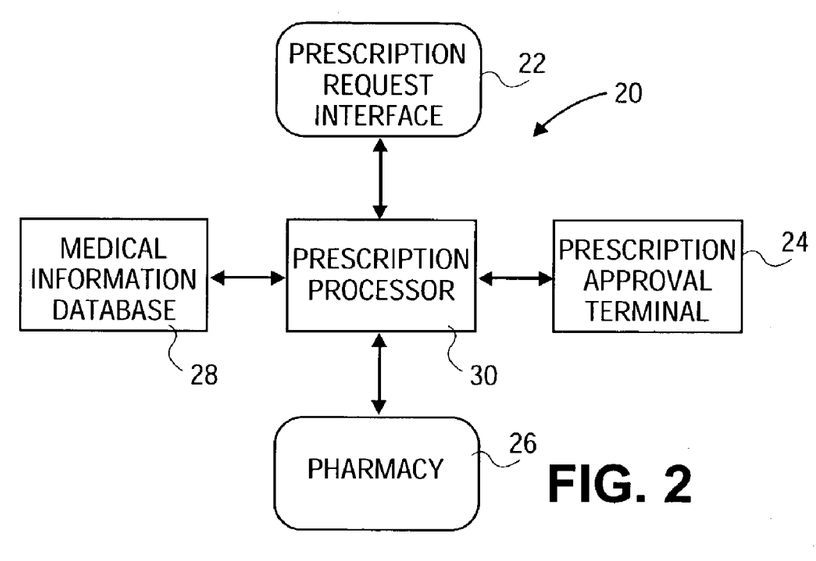
FIG. 2 is a block diagram of a pharmaceutical distribution system configured according to a first embodiment of the present invention.

FIG. 2 is a block diagram of a simplified example of the connectivity of a prescription distribution system 20 configured according to an embodiment of the present invention. The system 20 includes a prescription request interface 22, a prescription approval terminal 24, a medical information database 26, and a pharmacy 28, each coupled to a prescription processor 30. Each of these connections may be accomplished by any combination of wired or wireless connection. Each or any of the components 22, 24, 26, 28 and 30 of the system 20 may be located in a pharmacy 26, or in other remote locations such as the doctor's home or office, or even in a retail store, such as a grocery store, shopping mall, or any other place where it is desirable to have customers come. By attracting customers to fill their pharmaceutical needs, the retail store will also sell other products. Those of ordinary skill in the art will understand how to build an appropriate configuration of components for a given situation from the disclosure provided herein. Customer requests for prescriptions made through the prescription request interface 22 are transmitted electronically to and processed by the prescription processor 30. Information contained within the prescription request is compared with previous prescription request data within the medical information database 28, and is approved by a doctor reviewing the circumstances of each request on the prescription approval terminal 24. It should be understood that any or all of the components of the system may be implemented using conventional personal computers associated as a network, provided the prescription request interface 22 includes a camera associated therewith and programmed to take a picture of the user. In most embodiments, however, the prescription request interface 22 will be configured for general public use as a kiosk, and the prescription approval terminal 24 will more likely be configured as a personal computer. The doctor may approve the request and issue a prescription which is sent to the pharmacy 26 for distribution to the requestor as explained more fully hereafter. As used herein, "customer" and "requester" are occasionally interchanged, though "requestor" specifically refers to a customer who has requested a prescription.

Figure 3:
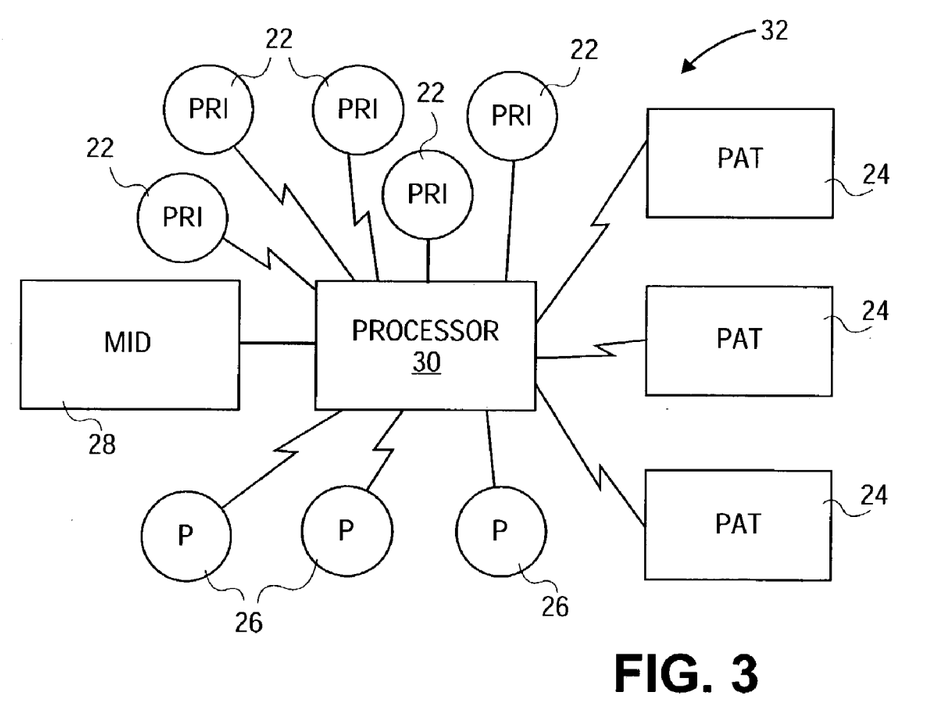
FIG. 3 is a block diagram of a pharmaceutical distribution system configured according to a second embodiment of the present invention.

FIG. 3 is a block diagram of a more comprehensive example of the connectivity of a prescription distribution system 32 configured according to another embodiment of the present invention. In this embodiment, the system 32 comprises a plurality of prescription request interface terminals 22 which may be located at one or more physical locations, such as at a plurality of remote pharmacies, or two or more may be located in close proximity such as within a shopping mall where many people may desire to use the terminals 22 simultaneously. Similarly, the system 32 of FIG. 3 comprises a plurality of prescription approval terminals 24 through which a plurality of doctors may approve prescriptions. A plurality of pharmacies 26 may be associated with the system 32 so that customers may select the pharmacy to which the prescription will be sent. To achieve benefit from embodiments of the present invention, a pharmacy 26 need only have a fax machine to receive a faxed prescription. The processor 30 may be configured to electronically send a fax to any pharmacy 26. However, in more advanced systems, such as that shown in FIG. 7, the pharmacy 26 may include a computer for receiving and reviewing the prescription electronically, and/or a printer, copier or fax machine for creating a hard copy of the prescription depending upon the needs of the pharmacy.

The pharmacy 26 of embodiments of the present invention may be adapted to send requested pharmaceuticals by carrier, such as is currently done with cyber-pharmacies, but with the added security of comparing the customer's requests with the medical information database 28 (including the shipping address and the requestor's picture). Software, such as that distributed by IQ Biometrix, Inc. of Fremont, Calif., exists which can compare facial images to determine identity like a finger print. Use of this software to compare faces of each requestor of prescription drugs may help to eliminate those who request multiple prescriptions using different names, and even different mailing addresses. Additionally, the requestor's picture may be included on the shipping label for use by the delivery person to ensure the medication is delivered to the correct person. Conventional cyber-pharmacy systems require a signature by the requester when the delivery is made. This, however, does not ensure security as the signator may be signing a different name. Use of this system, for example, would enable customers to have their prescriptions forwarded to and filled by a Canadian or other out-of-country pharmacy for shipment to the customers' homes in the United States.

Figure 4:
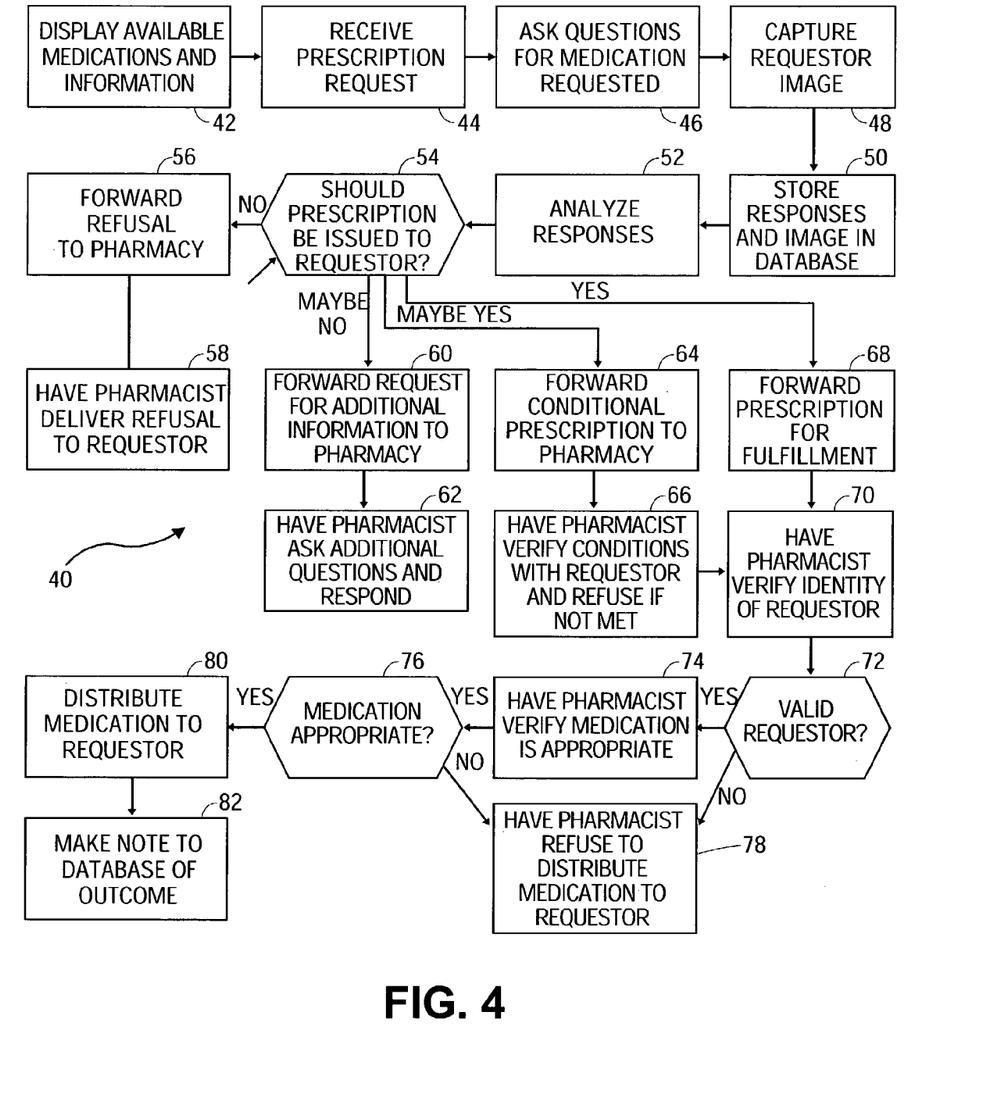
FIG. 4 is a flow chart of a method of distributing pharmaceuticals according to an embodiment of the present invention.

FIG. 4 includes a flow chart of a method of distributing pharmaceuticals according to a particular embodiment of the present invention. The method may be accomplished through a system having components such as those shown and described with reference to FIGS. 1-3. Information relating to prescription medications available through the system are displayed (Step 42). It is contemplated that the display terminal will be interactive so that potential customers can selectively review the available medications for the customer's particular problem, research possible side effects of each available drug, and make an educated and informed decision as to the specific drug for which the customer would like to request a prescription. Thereafter, the customer initiates, and the system receives, a prescription request (Step 44) for a particular prescription medication available through the system. Part of making the prescription request for particular embodiments of the invention involve sliding a credit card through a credit card reader and approving the charge to the credit card for the analysis of the prescription request by a doctor. As an additional security measure, the requestor's credit card billing address may be compared against the requestor's indicated home address, or a possible shipping address in certain embodiments, as a form of confirmation as to the identity of the requestor.

The customer is then presented with a questionnaire as part of the requesting process in which the requestor is asked a list of questions necessary for the particular medication requested (Step 46). Because only a limited number of drugs are available through the system, those establishing and monitoring the system can become experts in those particular drugs. This is unlike a conventional general practitioner doctor who is required to remember and recall all drugs available for all problems the doctor's patients may have. Particularly for lifestyle drugs, where an actual physical examination is generally not required, all of the potential drug interactions, health conflicts, and other concerns can be known and addressed through the questionnaire. There are typically a set of questions general to most drug requests, i.e. customer's date of birth, height, weight, known allergies, current medications, known medical problems, alcohol and cigarette intake, past surgeries, and the like. Additionally, there are a set of specific screening questions specifically directed to confirming that the particular medication requested is right for this requester. For example, and without limitation, with the genital warts drug Aldara®, the questions may include:

1) Do you have lesions that appear to be warts on or near your genital area?

2) Does your rash look more like that shown in Picture 1, 2 or 3? (Three pictures are shown)

3) Have you ever been diagnosed with Genital Warts, Human Papilloma Virus (HPV) or Venereal Warts?

A) If so, did you ever receive treatment for these warts?

B) If so, which of the following methods were used when you received treatment?(A list of possible treatments are shown)

C) Did you have success with any of those treatments?

D) Did you have any adverse reaction or reaction that prompted your doctor to discontinue treatment or advise you to not use that treatment in the future?

4) Have you had an HIV test?

5) Which of the following have you been tested for? (A list of other sexually transmitted diseases is shown)

6) Do you use any steroids?

7) Have you had an organ transplant?

Additional validation information may be requested to ensure that the requestor is legally eligible to receive the requested medication. For example, and without limitation, the validations may include, with a Yes or No response required for each one:

1) You are requesting the prescription medication(s) solely for your own personal therapeutic and medical needs, and not to distribute any of the medication to others.

2) You will promptly contact a local physician for any necessary medical intervention should a complication or concern result related to the use of a requested medication.

3) You realize that there are risks as well as benefits to any medication, even over-the-counter drugs. You have been informed of the possible effects, risks, and benefits of this medication.

4) You certify that you are 21 years of age or older.

5) You are permitted by law to receive these products in this region/country/locale.

6) You understand the side-effects of these pills.

7) You understand that you cannot have a prescription for this medication from more than one physician.

8) You certify that you are allowed by law to use the credit card you have selected below.

9) You understand that your credit card will be billed for this consultation and that if you choose to have this medication dispensed from a licensed pharmacist, this too will be billed to your account if your request is approved.

10) You certify that you have, and will, answer all questions truthfully.

11) You understand that in accordance with federal laws and rules, your personal medical and other information will be kept in confidence and will not be used for any commercial uses.

Additional information questions regarding the identity of the requestor may also be asked such as billing information, address, gender, etc., or for previous users of the system this information may be loaded from an associated database. The computerized medical questionnaire may be interactive, in that some answers from the consumer may determine which question will be asked next. One advantage of a computerized medical questionnaire is that it can embody at least as much knowledge as a human doctor to ensure technical safety in issuing the prescription.

At some time during the questions being asked of the requestor (Step 46), such as the point at which the requestor presses "send" or otherwise executes the request, a camera associated with the system will capture an image of the requester of the prescription (Step 48). The requestor's prescription request, answers to the questions, and image are then transferred to the medical information database (Step 50) for further reference. This request establishes a specific record of who requested the prescription, what medication was requested, and the requestor's assurances that the requester is entitled to receive and use the requested medication. It provides not only a confirmation that the requester was asked all of the appropriate questions and answered them appropriately, acknowledging all of the risks, but also that a specific photo record of who requested the prescription, answered the questions and later accepted the medication at the pharmacy. This record is one which is generally not created in a conventional doctor's office when prescribing a particular medication. The processor may make an initial determination from the response received as to whether the requestor should receive the prescription and pass that along with the requestor's responses. For example, and without limitation, if the requestor has frequently requested the same prescription medication without just cause, the same facial image is associated with more than one name, or more than one facial image is associated with the same name, this may be indicated to the doctor along with the prescription request. Also, if the database is aware of a conflicting prescription previously received by the requester which is not identified in the requestor's responses, if previous responses are inconsistent with current responses, or if the indications otherwise indicate that the requestor should not be using the requested medication, this may be indicated to the doctor along with the prescription request.

Notice of the prescription request is forwarded to a prescription approval terminal and the requestor's responses to the questions, along with any other database indications, are analyzed by a medical doctor (Step 52). A doctor reviewing prescription requests may approach the prescription approval terminal which displays a list of prescription requests to be reviewed. The doctor selects a prescription request to review and the prescription request is displayed at the terminal with the information needed for the doctor to make a decision. This information may include any or all of the requestor's responses to the questions, the requestor's image, the requestor's location and pharmacy request, and other information. The doctor then determines whether the prescription should be issued to the requester (Step 54). In determining whether the prescription should be issued (Step 54), the doctor may reference additional information such as a medical database including information about the patient's medical history, such as that provided by GE Medical or one of the many other medical database subscriptions, or may reference medical information database, text books or other informational resources to ensure that the prescription is appropriate for the requester.

If there is some reason the doctor believes the requestor should not receive the prescription, the doctor may indicate so at the doctor's terminal and a refusal to issue the prescription will be forwarded to the pharmacy (Step 56). In this case, the pharmacist may deliver the refusal to the requester at the pharmacy (Step 58). It is contemplated that this delivery may be verbal or merely a delivery of a refusal notice, and that the refusal may be a blank refusal or may include the reasons for the refusal and possibly recommendations for other possible medications. The pharmacist may note in the database or respond by fax, email or other method to indicate whether the requestor accepted the refusal, or make other notes as appropriate.

If the doctor's analysis indicates that the requestor probably should not receive the prescription but the doctor needs clarification, the doctor may forward a request for additional information to the pharmacy (Step 60) instead of a prescription. For example, if the requester indicates having previously used the requested or similar medication and having a negative reaction, the doctor may refuse the prescription and ask additional information to perhaps recommend an alternative. The pharmacist then can make the request to the requester for the additional information and respond (Step 62) to the doctor by phone or by return fax, email or other method. The pharmacist may note in the database or respond by fax or email to indicate the outcome, or make other notes as appropriate.

If the doctor's analysis of the prescription request indicates that the requester probably should receive the prescription but the doctor has some follow-up questions, the doctor may forward a conditional prescription to the pharmacy (Step 64) which indicates that the prescription may be distributed to the requester provided the requester satisfactorily answers the questions. For example, if the customer indicates having a rash but the rash could indicate a different problem as well, the doctor may ask follow-up questions to confirm the medication will be of help. The pharmacist may then verify the conditions imposed on the prescription with the requester (Step 66) and refuse the prescription if the conditions are not met. The pharmacist may note on the conditional prescription, in the database or respond by fax, email or other method to indicate the outcome, or make other notes as appropriate.

If the doctor's analysis of the prescription request indicates that there are no concerns with issuing the prescription, the doctor may forward a prescription for fulfillment (Step 68). Forwarding the prescription for fulfillment (Step 68), may include merely forwarding the prescription to the pharmacy. Alternatively, at the requester's request, the prescription may be forwarded by email to the requester (if an email address is provided), or forwarded to a different pharmacy at a remote location for pickup. The prescription may even be mailed to the requester for later fulfillment by the customer at a pharmacy of the customer's choice. Because the prescription includes the necessary confirmation and verification information on its face, the security benefits of the present invention will still be accomplished by sending the prescription directly to the requester. It will also be understood by those of ordinary skill in the art that the doctor may even forward a refusal, a request for additional information, or a conditional prescription directly to the requester, to a different pharmacy, or to another location of the requester's choice. This would allow the requester to answer additional information requests by the doctor through email, or enter into other communication with the doctor as required for a given situation. The prescription, particularly in cases where the prescription is not being sent directly to the pharmacy, may include a telephone number, or other contact method such as an Internet address and password, by which a pharmacy receiving the prescription may call and confirm the validity of that prescription, the requester, and that the prescription has not already been filled. Alternatively, a pharmacy connected to a common system with the medical information database may be able to access the database and confirm the validity of the prescription and requester for fulfillment. Additionally, though not required for practice of any embodiment of the present invention, the requester could be provided with a login and password through which the requester can check the status of the request online, or could check the status through a telephone number or help desk.

Once a prescription has been approved and forwarded to the pharmacy, including verified conditional prescriptions, the pharmacist may verify the identity of the requester (Step 70). This is accomplished by comparing the image of the requester, taken proximate the time of the initial prescription request, with the appearance of the person picking up the prescription, checking for a valid picture or other identification, and possibly asking some key questions from among the information provided by the requester during the initial prescription request. If it is determined that the requester is a valid requester (Step 72), the pharmacist may verify that the medication is appropriate for this requester (Step 74). The pharmacist may, of course, verify that the medication is appropriate before verifying the identity of the requester, but if the requester is not a valid requester, the effort of verifying the medication would be wasted.

In verifying that the medication is appropriate, the pharmacist may ask certain questions to the requester to confirm some of the responses provided by the requester during the initial request for the prescription. It is contemplated that to help the pharmacist and ensure appropriate questions are asked, the questions for the pharmacist to ask and confirm may be included as instructions for the pharmacist on the prescription. If the medication is not appropriate (Step 76) or if the requester is not a valid requester (Step 72), the pharmacist should refuse to distribute the medication to the requester (Step 78). The pharmacist may provide an explanation, and should make a note of the outcome on the prescription for return and entry into the medical information database.

If the medication is appropriate (Step 76), the pharmacist may distribute the medication to the requester (Step 80) and collect money for the prescription or indicate that the prescription will be charged to the requester's credit card. Whatever the result, refusal or issuance, the pharmacist may make a note to be entered into the database (Step 82) of the results to indicate that the prescription was filled, refused, or not picked up, and any other significant facts.

Pharmacists are extremely well trained to make many decisions about medications for patients. Some pharmacists are more knowledgeable about drug interactions and the appropriateness of particular drugs than many doctors. By relying upon the pharmacist as a secondary check for the prescription, instructing the pharmacist to ask particular questions relating to the requested medication, and engaging the pharmacist and requester of the medication in dialog relating to the requester's medical problem, the likelihood that the medication will be properly prescribed and used by the requester is significantly increased. Additionally, through the interaction between the pharmacist and the requester, the likelihood that the requester will ask additional questions about the drug and its use will increase. Each of these factors increase the safety of prescribing all forms of prescription drugs.

Conventionally, prescription refills are indicated on a prescription when it is initially granted, and a customer need only return to a pharmacy and request the refill. The refill is granted, generally, without any inquiry as to whether the medication was of any benefit to the customer, whether there are any negative side effects, whether the customer has begun taking any other medications which may conflict, or even whether the customer actually used the previous medication. To improve the security of refill prescription medication distribution, prescription refills may be requested and issued using the same systems and methods of the present disclosure with minimal modifications as explained below.

When a customer desires a refill for any prescription, the customer approaches a prescription request interface terminal, reviews the necessary information and requests a refill prescription (Step 44). The requester is asked a series of questions relating specifically to the request for the refill prescription (Step 46). For example, and without limitation, the requester may be asked whether the prescribed medication had the desired effects with respect to the requester's problem; whether the requester experienced any side effects from the medication; whether the requester used all of the previous prescription; whether the requester has started any new medications or been diagnosed with any relevant health problems; and other questions specifically related to the refill. The requester's picture is still taken (Step 48), and the information is still compared with and stored in the database (Step 50). The remainder of the process is the same except that the doctor's analysis (Step 52) includes additional and more relevant information, and the pharmacist now will ask questions relevant to the refill prescription prior to distributing the medication to the requestor (Step 80). Through follow-up questions when issuing prescriptions, the appropriateness of prescribed medications can be further confirmed and, if incorrect, can more readily be corrected.

With reference again to FIG. 1, the kiosk 2 of the present invention may also be used to fill existing prescriptions from remote locations. For example, and without limitation, there are circumstances when a patient would like to have a prescription filled by a pharmacy far away, such as in another country, or even on another side of town, but the patient either cannot travel to the pharmacy to have the prescription filled, wants the prescription mailed to the patient, or wants to have the prescription ready to pick up when the patient arrives at the pharmacy. In such cases, the patient can request through the kiosk 2 that an existing prescription be filled. In such cases, the customer may fill out basic contact and payment information at the kiosk display 10, hold the existing prescription in front of the camera 14 or place it in an appropriately configured holder before the camera 14, and the camera 14 will capture an image of the prescription to send to a pharmacy or for fulfillment at a remote location. A photograph of the requestor may optionally be taken and added to the prescription for added security in accordance with previous embodiments of the invention described herein.

As will be clear to those of ordinary skill in the art, the medical information database used in embodiments of the present invention may be configured in many different ways and may include any number of different types of information. Those of ordinary skill in the art will be readily able to design and build an appropriate database depending upon the needs of a particular system and the information desired to be stored and retrieved by system administrators. In particular embodiments of the present invention, each request for a prescription along with all responses and all relationships between requests may be tracked, queried and searched. The usefulness of the database in providing security against fraudulent prescription requesters is dependent, in part, upon the ability to search and compare existing records.

Figure 5:
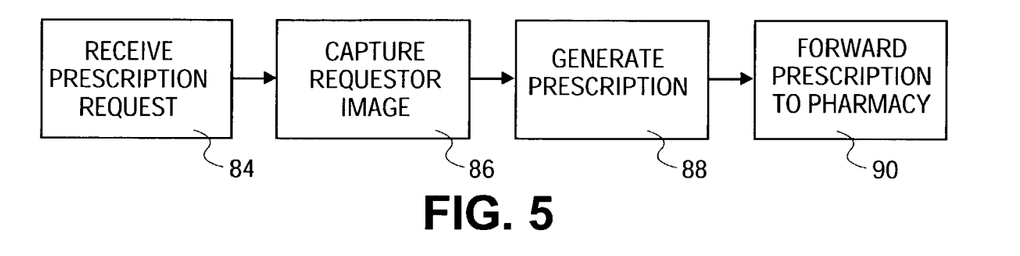
FIG. 5 is a flow chart of a method of generating a prescription according to an embodiment of the present invention.

FIG. 5 includes a flow chart of a simplified method of generating a prescription according to an embodiment of the present invention. A prescription request is received (Step 84) through a system such as that shown and described with reference to FIGS. 1-3 or otherwise. An image of the requestor proximate the time of the request is captured (Step 86) and saved. A prescription is generated which includes the captured image of the requestor (Step 88), and the prescription with the image is forwarded to the pharmacy to be filled (Step 90). As an alternative to forwarding the prescription to the pharmacy to be filled (Step 90), as explained previously with reference to FIG. 4, the prescription, in any form or of any type, refusal, or request for additional information may be forwarded to the requester directly by any method, or to a different pharmacy or other location as requested by the requestor.

Figure 6:
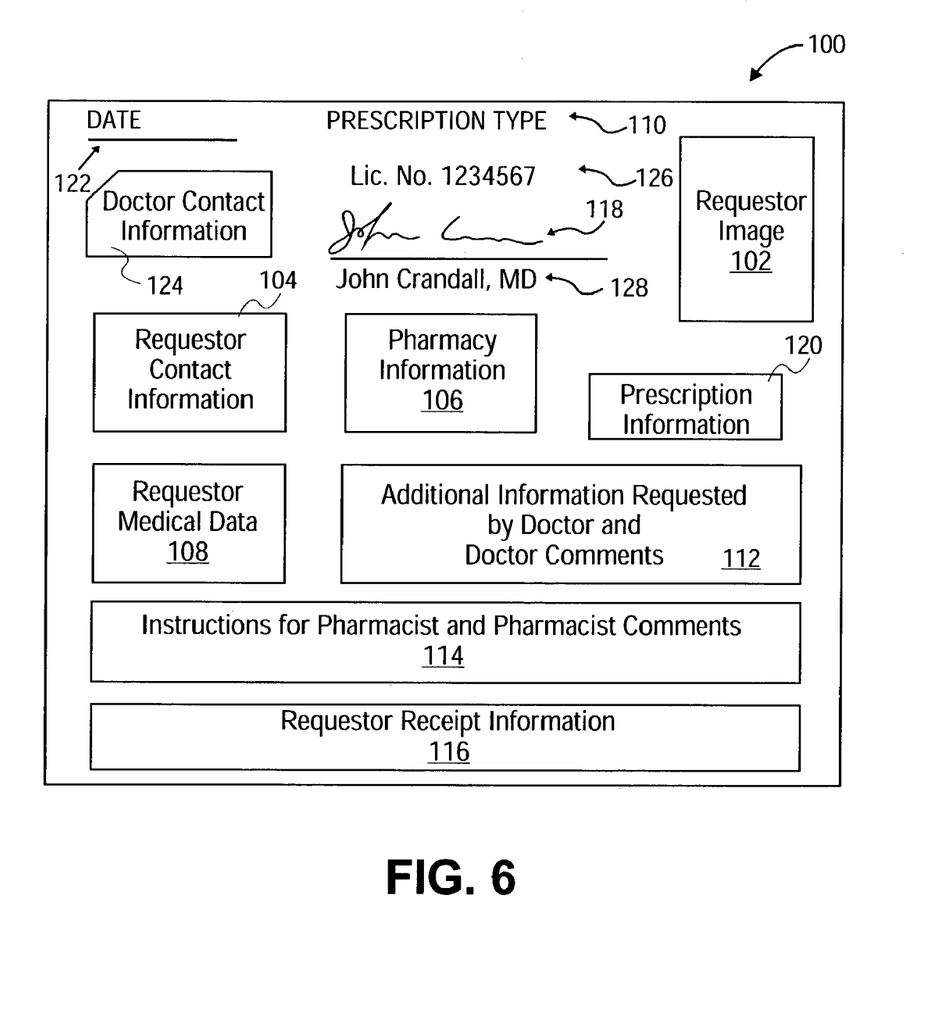
FIG. 6 is a prescription generated according to an embodiment of the present invention.

FIG. 6 illustrates an example of a prescription 100 generated according to a particular embodiment of the present invention. A prescription 100 generated according to specific embodiments of the present invention may include any or all of the elements described with reference to FIG. 6, in whatever combination is necessary or desired for a particular system. The prescription 100 shown and described with regard to this particular embodiment is intended as a non-limiting example. A prescription 100, or conditional prescription, configured according to the present embodiment, includes an image of the requestor 102, the requestor's contact information 104, information regarding the pharmacy 106 to which the requester indicated the prescription should be sent, pertinent medical data 108 relating to the requestor, and a prescription type 110 (i.e. Prescription or Conditional Prescription). The prescription 100 also includes a section for comments or additional questions from the doctor 112, a section for specific instructions to the pharmacist and comments by the pharmacist 114, and a section for payment and perhaps delivery receipt information for the requester 116. Like a conventional prescription, a prescription 100 configured according to the embodiment of FIG. 6 also includes a doctor's signature 118, prescription information 120 regarding the medication, dosage and perhaps refills prescribed, and a date 122 for the prescription. Embodiments of the prescription may also include the doctor's full contact information 124, license number 126, and title below the signature 128 for clarity.

Figure 7:
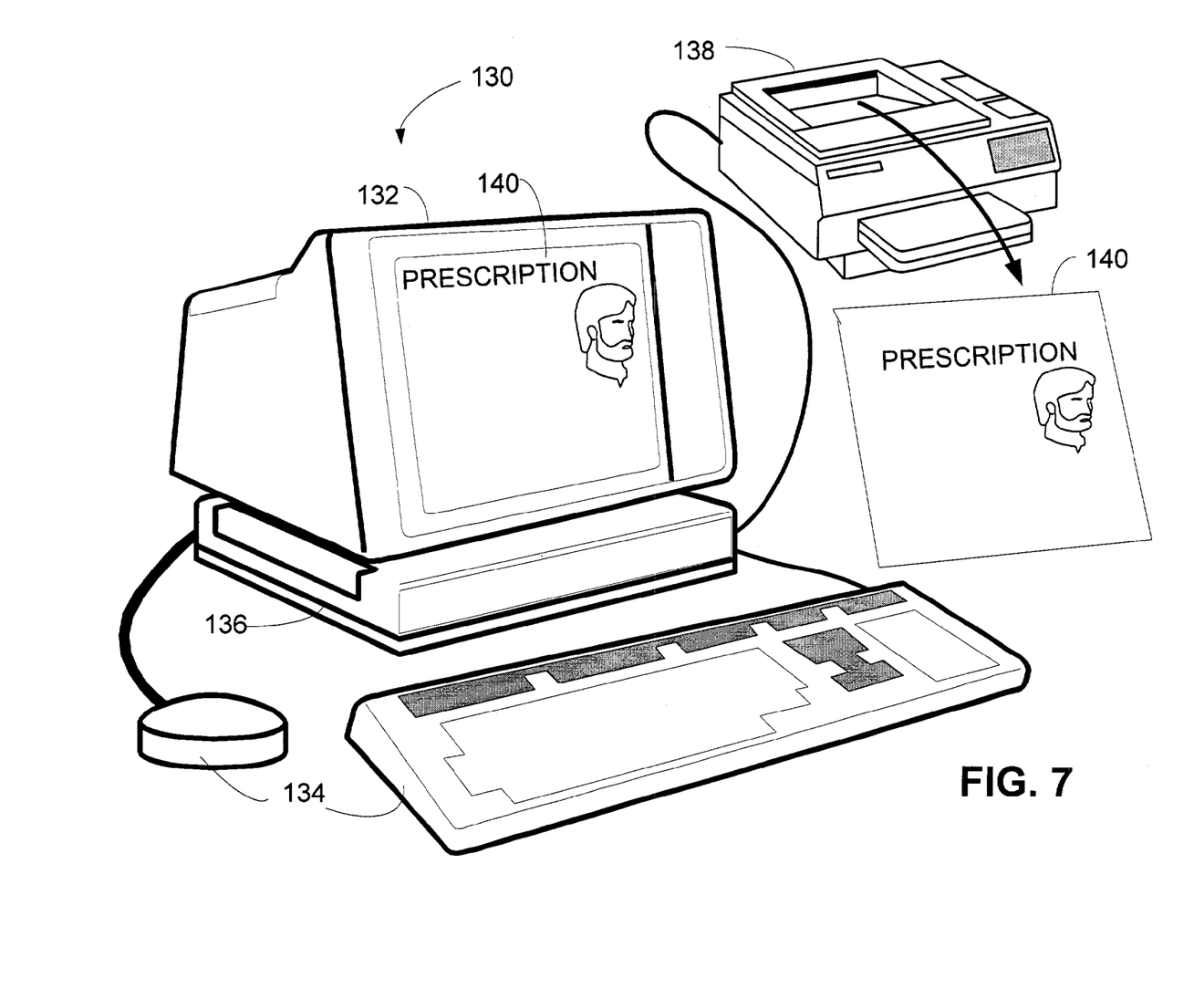
FIG. 7 is a pharmacy prescription terminal according to an embodiment of the present invention.

FIG. 7 illustrates an example of a pharmacy prescription terminal 130 for use by a pharmacy for receiving, reviewing and responding to prescription requests. The prescription terminal 130 includes a display 132, one or more input devices 134 such as a keyboard and mouse, a central processing unit 136, and a printing device 138 associated with the central processing unit 136 for generating hard copy versions of prescriptions, prescription refusals and other communications from the prescription distribution system. Each prescription 140, may be displayed on the prescription terminal 130 and/or printed at the printing device 138. Though not explicitly shown in FIG. 7, it will be understood that the pharmacy prescription terminal 130 is associated with a prescription distribution system processor as explained earlier herein. Pharmacists may review prescriptions on the prescription terminal 130, respond to requests by doctors through the prescription terminal 130, and enter notes and comments into the prescription terminal 130 as needed to implement the methods of establishing a secure prescription drug distribution system according to embodiments of the present invention.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. For example, it should be clear to those of ordinary skill in the art from the present disclosure that many aspects of the present system and prescriptions may be used independently to increase the security and accuracy of the prescription drug process. For additional example, and without limitation, the use of a requestor's image on the prescription, while significantly decreasing the likelihood for fraud, is not required in particular embodiments of the invention because merely the increased interaction between the pharmacist and the requester through indicating specific instructions for the pharmacist and questions for the pharmacist to ask the requestor will decrease the likelihood for fraud and increase the likely appropriateness and success of the medication requested. While specific embodiments of the present invention are described in relation to lifestyle drugs, it will be understood that many of the safeguards apply to all prescription drugs and similar systems or portions of similar systems may be implemented in doctors' offices and the like to enable the safeguards, such as the patient photo and follow-up questions by the pharmacist, to be implemented even where an actual physical examination is required.

The invention claimed is:

1. A prescription drug distribution system comprising:
 a prescription drug request interface displaying a description of a plurality of prescription drugs; and
 a camera associated with the prescription drug request interface and configured to capture an image of a customer at the prescription drug request interface;
 wherein the prescription drug request interface is configured to receive a request for a prescription drug from the customer through an interface input, capture a facial image of the customer requesting the prescription drug proximate a time of the request through the camera, and forward the prescription request to a medical doctor remote from the prescription drug request interface, the prescription request including the image of the customer requesting the prescription drug;
 wherein the prescription drug request interface is further configured to receive responses from the customer to a plurality of medical questions related to the prescription drug requested;
 wherein the system is configured to generate a prescription in response to the request, the prescription comprising the image of the customer requesting the prescription drug and at least a sub-set of the customer's responses to the plurality of medical questions related to the prescription drug requested.

2. The prescription drug distribution system of claim 1, further comprising a printer at the pharmacy configured to print the prescription.

3. The prescription drug distribution system of claim 1, further comprising a display at the pharmacy configured to display the prescription.

4. The prescription drug distribution system of claim 1, further comprising a prescription request review terminal configured to display the prescription request and receive approval for the request from the medical doctor.

5. The prescription drug distribution system of claim 1, further comprising a database configured to store information associated with a prescription and a database monitor configured to identify potential prescription abuses by the customer.

6. A method of distributing a prescription medication to a patient requesting the prescription medication, the method comprising:
 receiving a request through a computer terminal for a prescription medication from a patient;
 gathering information about the patient's identity through the computer terminal, wherein the information about the patient's identity comprises a photograph of the patient's face taken through a camera associated with the computer terminal proximate a time the patient requests the prescription medication;
 gathering information through the computer terminal about a medical condition of the patient relating to the prescription medication through an electronic questionnaire;
 analyzing the information about the patient's medical condition through a medical doctor to determine if the requested medication is appropriate for the patient and the patient's medical condition;
 issuing a prescription from the medical doctor to a pharmacy for the medication requested by the patient, the prescription comprising the photograph of the patient's face; and
 using the photograph of the patient's face to verify the identity of the patient, and confirming at least a portion of the patient's information about the medical condition with the patient at the pharmacy before dispensing the medication.

7. The method of claim 6, further comprising obtaining information about other prescriptions recently obtained by the patient.

8. The method of claim 7, wherein obtaining the information about other prescriptions recently obtained by the patient comprises searching a prescription database for matching identity information.

9. The method of claim 7, further comprising denying the patient's request for the prescription medication if the patient is requesting one of a duplicate and a conflicting medication.

10. The method of claim 6, wherein requesting the prescription medication and gathering the information are accomplished using an interactive computer terminal.

11. The method of claim 10, wherein gathering the information using an interactive computer terminal comprises gathering the information using an interactive computer terminal associated with a digital camera, the digital camera operable to take the photograph of the patient's face when time the patient's identity information is gathered.

12. The method of claim 11, wherein gathering the information using an interactive computer terminal comprises using at least one of:
 a personal computing device having an Internet connection;
 a computer located at the pharmacy and having at least one of an Internet connection and an Intranet connection; and
 a computer located in a retail store and having at least one of an Internet connection and an Intranet connection.

13. The method of claim 10, wherein gathering the information using an interactive computer terminal comprises gathering information using a computer installed in a kiosk with a digital camera.

* * * * *